United States Patent
Tanghoej et al.

(10) Patent No.: US 8,679,092 B2
(45) Date of Patent: *Mar. 25, 2014

(54) CATHETER ASSEMBLY

(75) Inventors: Allan Tanghoej, Kokkedal (DK); Lars Boegelund Jensen, Roedovre (DK)

(73) Assignee: Coloplast A/S, Humlebaek (DK)

( * ) Notice: Subject to any disclaimer, the term of this patent is extended or adjusted under 35 U.S.C. 154(b) by 344 days.

This patent is subject to a terminal disclaimer.

(21) Appl. No.: 13/078,012

(22) Filed: Apr. 1, 2011

(65) Prior Publication Data

US 2011/0213343 A1    Sep. 1, 2011

Related U.S. Application Data

(63) Continuation of application No. 12/370,627, filed on Feb. 13, 2009, now Pat. No. 8,002,766, and a continuation of application No. 10/482,229, filed on Dec. 29, 2003, now Pat. No. 7,517,343.

(30) Foreign Application Priority Data

| Jun. 29, 2001 | (DK) | ................................. 200101041 |
| Sep. 24, 2001 | (DK) | ................................. 200101386 |
| Dec. 13, 2001 | (DK) | ................................. 200101869 |
| Dec. 13, 2001 | (DK) | ................................. 200101870 |
| Apr. 17, 2002 | (DK) | ................................. 200200569 |
| Apr. 17, 2002 | (DK) | ................................. 200200570 |
| Jun. 13, 2002 | (DK) | ................................. 200200895 |
| Jun. 28, 2002 | (WO) | ..................... PCT/DK02/00447 |

(51) Int. Cl.
*A61M 5/32* (2006.01)
*A61M 27/00* (2006.01)
*A61F 5/44* (2006.01)

(52) U.S. Cl.
USPC ............................ 604/544; 604/349; 604/163

(58) Field of Classification Search
USPC ..................... 604/544, 39–42, 363, 265–265, 604/171–172, 327, 331, 349–350; 206/363
See application file for complete search history.

(56) References Cited

U.S. PATENT DOCUMENTS

| 3,154,080 A * | 10/1964 | Rowan et al. ................. 604/171 |
| 3,335,723 A | 8/1967 | Waldman |
| 3,556,294 A * | 1/1971 | Walck et al. .................. 206/210 |
| 3,648,704 A * | 3/1972 | Jackson ........................ 604/172 |
| 3,750,875 A * | 8/1973 | Juster ........................... 206/364 |
| 3,854,483 A | 12/1974 | Powers |
| 3,934,721 A | 1/1976 | Juster et al. |
| 4,026,298 A | 5/1977 | Grausz |
| 4,062,363 A * | 12/1977 | Bonner, Jr. .................... 604/171 |
| 4,140,127 A * | 2/1979 | Cianci et al. .................. 604/171 |
| 4,235,232 A * | 11/1980 | Spaven et al. ................. 604/178 |

(Continued)

OTHER PUBLICATIONS

Office Action mailed on Mar. 31, 2011 in U.S. Appl. No. 12/698,241.

*Primary Examiner* — Kevin C Sirmons
*Assistant Examiner* — Andrew Gilbert
(74) *Attorney, Agent, or Firm* — Coloplast Corp., Coloplast A/S; Nick Baumann

(57) ABSTRACT

A catheter assembly is provided. The catheter assembly includes a urinary catheter adapted for insertion into a urethra and a catheter package sized to receive the urinary catheter. The urinary catheter is configured to project from the catheter package to accommodate insertion into the urethra.

1 Claim, 11 Drawing Sheets

(56) References Cited

U.S. PATENT DOCUMENTS

| | | | |
|---|---|---|---|
| 4,805,611 A * | 2/1989 | Hodgkins | 128/207.14 |
| 4,850,350 A * | 7/1989 | Jackson | 128/207.16 |
| 5,041,085 A * | 8/1991 | Osborne et al. | 604/541 |
| 5,147,341 A * | 9/1992 | Starke et al. | 604/349 |
| 5,167,646 A * | 12/1992 | Swafford | 604/275 |
| 5,167,647 A | 12/1992 | Wijkamp et al. | |
| 5,242,398 A * | 9/1993 | Knoll et al. | 604/103.05 |
| 5,454,798 A * | 10/1995 | Kubalak et al. | 604/328 |
| 5,715,815 A * | 2/1998 | Lorenzen et al. | 128/207.14 |
| 5,951,929 A | 9/1999 | Wilson | |
| 6,004,305 A * | 12/1999 | Hursman et al. | 604/328 |
| 6,149,996 A | 11/2000 | Helgerson | |
| 6,158,912 A | 12/2000 | Bouix | |
| 6,217,569 B1 * | 4/2001 | Fiore | 604/544 |
| 6,245,047 B1 | 6/2001 | Feda et al. | |
| 6,355,004 B1 | 3/2002 | Pedersen et al. | |
| 6,602,244 B2 * | 8/2003 | Kavanagh et al. | 604/544 |
| 7,311,698 B2 * | 12/2007 | Tanghoj et al. | 604/544 |
| 7,380,658 B2 | 6/2008 | Murray et al. | |
| 7,517,343 B2 * | 4/2009 | Tanghoj et al. | 604/544 |
| 7,682,353 B2 | 3/2010 | Tanghoj et al. | |
| 7,922,712 B2 * | 4/2011 | Tanghoj et al. | 604/544 |
| 8,282,624 B2 * | 10/2012 | Tanghoej et al. | 604/544 |
| 2008/0045921 A1 | 2/2008 | Anderson et al. | |

* cited by examiner

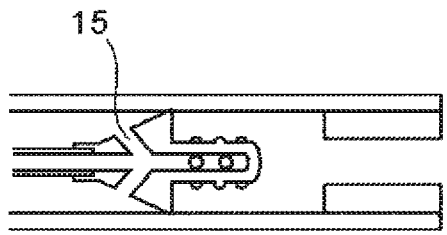
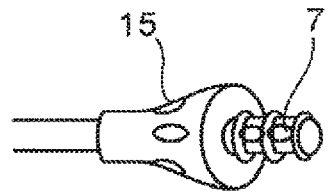
Fig. 1a     Fig. 1b
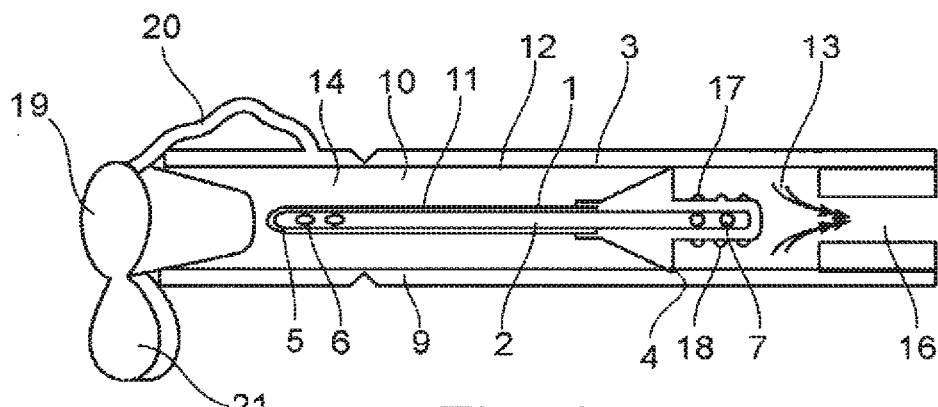
Fig. 1c
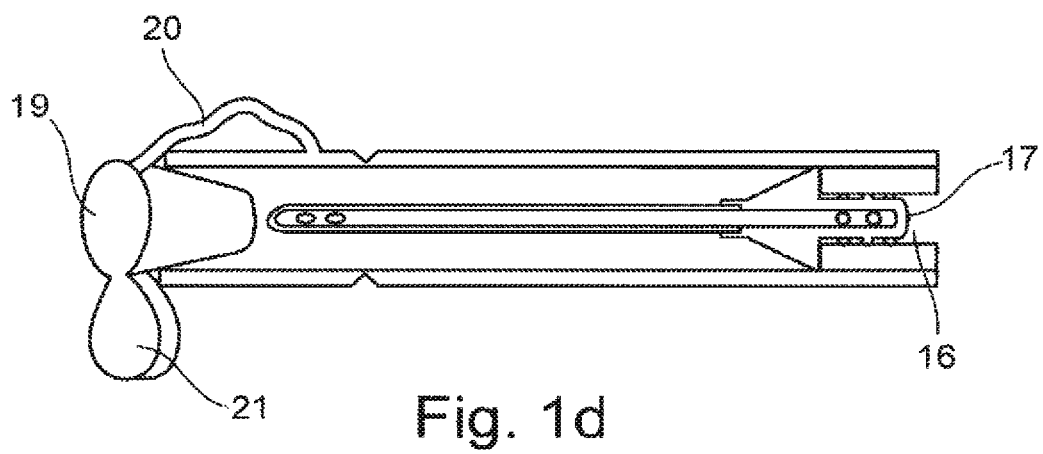
Fig. 1d

CATHETER ASSEMBLY

FIELD OF THE INVENTION

The present invention relates to a urinary catheter assembly comprising a package allowing for storage of the catheter and for contamination free insertion of the catheter into a natural or an artificial urinary canal of an individual.

BACKGROUND OF THE INVENTION

Catheters for draining the bladder are increasingly used for intermittent as well as indwelling or permanent catheterisation. Typically, catheters are used by patients suffering from urinary incontinence or by disabled individuals like para- or tetraplegics who may have no control permitting voluntary urination and for whom catheterisation may be the way of urinating.

Typically, catheters are provided to the user enveloped in a completely sealed and sterilised package. During use and prior to insertion, the catheter is typically removed completely from the package whereby a potential contamination of the catheter may occur, e.g. if the user unintentionally touches the catheter or if the catheter touches surrounding obstacles, e.g. a toilet seat, a wash basin etc. Catheter packages and assemblies of catheters and packages exist, wherein both a proximal end and a distal end of the package may be opened, thus allowing for draining the urine through a catheter which is still at least partly enveloped in the package. Thereby, the user may urinate without completely exposing the catheter and the risk of contamination is reduced. However, since there is a clearance between the inner surface of the catheter package and the outer surface of the catheter itself, urine may flow backwards in the package in a direction opposite to the flow direction inside the catheter. An unwanted situation is that urine or other liquid substances, e.g. a lubricant or water applied to the catheter for the purpose of reducing the surface friction, contaminates the user of the catheter and/or the surroundings.

Since only the inserted part of the catheter is exposed from the package prior to insertion of the catheter, another unwanted situation may be that the user unintentionally forgets to open the other end of the catheter package. An amount of urine may thereby build up in the catheter package and possibly cause a back-flow in the catheter tube. In this case, there is a risk of severe contamination of the surroundings and also a possibility of back-flow into the bladder.

Moreover, existing catheters are provided in various sizes. As an example, catheters, which are relatively long are offered for male individuals whereas relatively short catheters are offered for female individuals. Evidently, more variants of the same product imply problems and costs for the providers of urinary catheters.

Catheter assemblies comprising a catheter and a package which includes an amount of a liquid substance, e.g. a lubricant for a conventional catheter or a liquid swelling medium for a hydrophilic catheter exist. Some of the existing packages provide a combination between a storage volume for sterile storage of the catheter and a reservoir for collection of liquid substances, e.g. for collection of friction reducing substances or for collection of urine. Typically, there is a large disproportion of the storage capacity necessary for storing the friction-reducing substance and the urine, respectively. Accordingly, the known catheter assemblies of this kind are provided with a relatively small storage container for storing the friction-reducing substance inside the relatively large urine reservoir. It is a disadvantage of the known assemblies that the user, prior to insertion of the catheter into the urinary canal, will have to rupture the storage container in order to achieve a reduced surface friction of the catheter. Especially, it is a disadvantage in the event that the catheter is a hydrophilic-coated catheter. In this case, the user would need to open the storage container to allow a liquid swelling medium stored therein to activate the coating and subsequently wait for at least 30 seconds in order to complete the activation of the coating prior to the insertion of the catheter.

DESCRIPTION OF THE INVENTION

It is an object of the present invention to overcome the above described disadvantages of the known catheter assemblies by providing a urinary catheter assembly which, according to a first aspect of the invention, allows the insertion of a catheter into a urinary canal directly from the package without touching the catheter and without contamination of the surroundings. The assembly comprises:

a urinary catheter defining a conduit and having a proximal end adapted for insertion into a urinary canal of an individual and an opposite distal end, and a catheter package having a hose with a cavity for accommodation of the catheter and, in a proximal end thereof, a catheter outlet adapted to dismantle the proximal end of the catheter from the catheter package, and sealing means adapted to provide a substantially liquid tight seal between the catheter package and the urinary catheter, while the catheter is being dismantled from the package.

Due to the sealing means, the catheter may be dismantled from the package until a catheter length sufficient for the opening of the bladder is exposed. At this stage, urine may be drained into the proximal end of the catheter and from the catheter into the hose and through the hose to a place of disposal, e.g. to the lavatory. The hose of the package thus function as an extension of the catheter allowing the user e.g. to reach the lavatory without having to stand up from a wheelchair or a bed etc. Since the sealing means seals between the catheter and the hose, it is ensured that urine does not flow back between the hose and the catheter and drains out of at the end of the package from which the catheter is being dismantled, i.e. the end of the package which extends in a direction towards the individual. Evidently, draining of fluids through this end may cause contamination of the surroundings and/or the individual.

The sealing means may be provided in the proximal end of the package, e.g. constituting a closure for the proximal end of the package. As an example, the closure may have a rupturable portion with a shape which matches the outer cross-sectional shape of the catheter. When the catheter is removed through the rupturable portion, the closure will sealingly surround the catheter while the catheter is being dismantled. The cavity is thereby defining a receptacle between the catheter and the hose. The receptacle may e.g. be used for storage of a friction-reducing substance.

The sealing means may also be arranged between an outer surface of the urinary catheter and an inner surface of the hose. As an example, the sealing means may be provided in the form of a sliding seal adapted to move in relation to one of either the inner surface of the hose, the outer surface of the catheter or both, while still providing a substantial liquid tight passage therein between. The cavity thereby defines an upper receptacle located near the proximal end of the package and an oppositely located lower receptacle between the catheter and the hose. The upper receptacle may advantageously be used for storing a friction reducing substance for treatment of at least the proximal end of the catheter in the package.

The catheter or at least a section thereof may be provided with a hydrophilic surface, either in the form of a coated catheter or in the form of a catheter made throughout of a hydrophilic material. When treated with a liquid swelling medium, such a surface will provide an excellent lubrication for the insertion and also provide compatibility with the body tissue.

The catheter may also be of the traditional type wherein the low friction character is obtained by application of a lubricant different from water, e.g. a silicone based lubricant, the lubricant being applied to at least a section of the catheter.

The liquid swelling medium for a hydrophilic surface may be provided in the package, especially in the upper storage compartment, near the proximal end of the catheter, when the catheter is arranged in the package. Thereby, the low friction character will be initiated already when the catheter is being arranged in the package. The liquid swelling medium may simply be a saline solution, a bactericidal solution capable of swelling the hydrophilic surface and capable of keeping the surface in a sterile condition or it may be any suitable liquid swelling medium. The swelling may also be initiated already before packaging of the catheter, the catheter then being packed in a substantially gas impermeable package for conservation of the moistened surface. Furthermore, the liquid swelling medium may be provided in a capsule or container directly within the hose member together with the catheter for swelling of the hydrophilic material immediately prior to the insertion.

It is an advantage to provide the catheter package in a material which is at least substantially gas and water impermeable, which is durable to at least moderate external conditions such as temperature variations and light. The material should at least substantially maintain its properties over a period of up to 12 or more months, e.g. up to 24 month. The catheter package and/or the hose member could therefore preferably be made from silicone or a thermoplastic elatomeric material, other thermoplastic materials, curable elastomeric materials, polyamide resins or elastomers or any mixture thereof, i.e. the group may comprise materials like, PA, PP, PVC, PU, PE, latex, and/or Kraton™. All parts of the catheter package may be made from two foils of a sheet material joined along edges, e.g. by melting or gluing or in any other way be adhesively bonding the foils together. The package may also be made from an extruded substantially tubular member being closed in both ends. The foil may advantageously be made from laminates of different materials. One layer may e.g. be made from aluminium or similar metal or from a composition of metals, e.g. comprising aluminium. Such a layer will provide a completely gas-impermeable package.

The proximal end and the distal end of the catheter package could be provided with an even structure. However, it will be preferred that the proximal end of the package is provided with opening means adapted to remove the proximal end of the catheter. Similarly, the distal end of the package may be provided with opening means adapted specifically for draining fluid substances from the package. The fluid substances may either be a friction-reducing medium or urine.

Preferably, the hose member is an elongate and/or tubular member adapted to accommodate at least a major part of the catheter. If the catheter is of the kind which develops a low friction surface character upon treatment with a liquid medium or substance, it may be an advantage to provide the liquid medium in the package and preferably in the hose member. The catheter will thereby be treated already upon removal of the catheter from the package. For this purpose, the hose member may preferably be adapted to relatively closely enclose the catheter. As an example, the inner diameter or the cross-sectional area within the inner surface of the hose member may be in the range of 1.1-2 times the outer diameter or the cross-sectional area within the outer surface of the catheter, such as 1.2-1.9 times, such as 1.3-1.8, such as 1.4-1.7, such as 1.5-1.6, such as in the size of 1.55 times the outer diameter or the cross-sectional area of the catheter. Alternatively, the liquid medium may be contained in a pouch connected to the package. The pouch may e.g. constitute a closure for closing either the proximal or the distal end of the package. Preferably, the pouch is integrated in a closure for closing the proximal end of the package, which end is located near the proximal end of the catheter.

If the catheter is a hydrophilic catheter, i.e. if the catheter is either coated with a hydrophilic coating or made completely from a hydrophilic material, the liquid substance may be water or a water/saline solution. If the catheter is of the traditional type having a primarily hydrophobic surface, the liquid substance may be a lubricant, e.g. based on silicone.

The sealing means could be provided in the form of an obstruction which substantially prevents a liquid substance to pass between the inner surface of the package and outer surface of the catheter. The sealing means thus divides the space confined between the catheter and the hose member into an upper receptacle in the direction towards the proximal end of the catheter and package and a lower receptacle in the direction towards the distal end of the catheter and package.

As an example, the sealing means could be provided as a radially outwardly extending protrusion of the outer surface of the catheter or as an inwardly extending protrusion of the inner surface of the hose member, e.g. in the form of a resilient vane adapted to contact the inner surface of the hose member or outer surface of the catheter, respectively. The outwardly extending protrusion of the catheter should in this respect be understood either as a protrusion connected to the catheter or a protrusion formed directly on the surface of the catheter. As an example, the catheter may be connected with a plug member which plug member is provided with vanes adapted to slide along the inner surface of the hose or at least parts thereof. Similarly, the inwardly extending protrusion of the hose should be understood either as a protrusion connected to the hose or a protrusion formed directly on the inner surface thereof.

Two or more radially outwardly or inwardly extending protrusions of the outer or inner surfaces of the catheter and/or the hose member, will provide an even better sealing against flow of liquid substances between the two compartments. By providing the at least two radially inwardly extending protrusions of the inner surface of the hose member with different radial sizes, a further sealing effect will be achieved.

According to a preferred embodiment, the sealing means comprises a ring-shaped member arranged between the inner surface of the hose member and the outer surface of the catheter. As an example, a regular ring-shaped gasket may be placed inside the hose member. Preferably, the member is loosely arranged so that it is allowed to move back and forth inside the hose. As an example, the ring-shaped member may be provided with a clearance against the hose member and against the catheter so that liquid substances are substantially prevented from passing the ring-shaped member and so that the ring-shaped member is still allowed to be shifted longitudinally back and forth in the catheter package.

The ring-shaped member may preferably be adapted to co-operate with an inwardly extending protrusion of the inner surface of the hose member or with an outwardly extending protrusion of the catheter.

The distance from the distal end of the urinary catheter to the position of the sealing means may preferably be provided between 0 and 100% of the total distance between the distal end of the catheter and the proximal end of the catheter, such as 0%, such as 10%, such as 20%, such as 30%, such as 40%, such as 50%, such as 60%, such as 70%, such as 80%, such as 90%, such as 99%.

In general, the problems of introducing a catheter into urethra depend not only on the size of the introduced part of the catheter but also on the slipperiness of the introduced part. As previously mentioned, the catheter or at least a part of the catheter adapted for insertion into urethra or an artificial urinary canal may often be provided with a surface slipperiness for easy and safe insertion. However, it has been found that the slippery surfaces are difficult to handle, not least for a user having reduced dexterity. It is therefore an important aspect of the present invention to allow the user to manipulate the catheter by touching only the catheter package and only to expose a length of the catheter, which is necessary for opening the bladder. Preferably, the sealing means is arranged so as to seal between the outer surface of the catheter and the inner surface of the hose over a certain dismantling length. This will allow the user of the catheter to withdraw the catheter at least partly from the package, e.g. by pulling the proximal end of the catheter out of the catheter package. Meanwhile, the sealing between the catheter and the package remains. The feature allows that a catheter type of one length can be supplied both to male and female users. The user only needs to withdraw a length of the catheter from the catheter package necessary for opening the bladder, i.e. approximately 50-90 mm. for female users and approximately 180-250 mm. for male users.

The sealing means and/or the hose member may preferably be provided so that no passage is formed between the outer surface of the catheter and the inner surface of the hose member while the catheter is being dismantled over a first dismantle period, thus preventing fluid from passing between the urinary catheter and the hose member when the sealing means is positioned within said first period.

In order not to contaminate the surroundings with friction-reducing substances, it is an advantage to allow such a substances which may possibly be stored in the upper receptacle to drain down into the lower receptacle before dismantling the catheter through the proximal end of the package. The sealing means and/or the hose may therefore preferably be provided so that a clearance is defined between the outer surface of the urinary catheter and the inner surface of the hose member over a second dismantling period, thus allowing a fluid to pass between the urinary catheter and the hose member when the sealing means is positioned within said second period. As the catheter is being removed from the package, the catheter enters the second dismantling period. Any liquid substance contained in the upper receptacle is thereby drained down into the lower receptacle and it is thereby avoided that the substance unfortunately is released through the proximal end of the package.

The length of the first dismantling period may preferably constitute between 0 and 100% of a total length of the package, such as 0%, such as 10%, such as 20%, such as 30%, such as 40%, such as 50%, such as 60%, such as 70%, such as 80%, such as 90% or such as 100%.

According to one embodiment, the substantially liquid tight seal is provided continuously between the catheter package and the catheter over the first dismantle period. However, the liquid tight seal may also be provided discontinuously, e.g. stepwise.

Most catheters are provided with a surface which, when treated with a friction-reducing substance, exhibits a low friction surface character. Accordingly, it is an advantage that the package defines a liquid tight wetting pocket for treatment of the surface part with such a substance. If the catheter is hydrophilic or at least is provided with a hydrophilic surface coating on at least the proximal end thereof, the substance would typically be a water based solution, e.g. a saline solution. If the catheter is not hydrophilic, the substance may e.g. be a silicone based solution.

It is a further advantage to provide the assembly with an amount of the substance which is sufficient for effecting a treatment of at least a part of the catheter surface. As an example, the treatment may be performed on a first part of the catheter, which part is adapted for insertion into the urethra. The treatment may advantageously take place in the upper receptacle.

According to a preferred embodiment of the invention, the substance is contained in a pouch connected to the assembly. The pouch may as an example constitute a closure for closing one of either the proximal or distal ends of the package. Preferably, at least the proximal end of the package, i.e. the end located near the proximal end of the catheter, is closed by a pouch, so that the substance can be squeezed out of the pouch and onto the proximal insertable catheter end. According to another preferred embodiment, the substance is applied to the receptacle or at least the upper receptacle during the assembling process. The low friction surface character of the catheter is thereby initiated already from the time when the catheter assembly is produced. The package is therefore preferably formed with a wall of a substantially gas impermeable material so as to allow long time preservation of the catheter and a liquid substance in the package.

It is an advantage to provide the package with an opening for draining a liquid substance out of the package. As an example, the opening may be used for draining out surplus liquid swelling medium remaining in the package after treating a hydrophilic catheter. As another example, the opening may be used for draining urine out of the package. For this purpose, the opening is preferably provided in the distal end of the package. During use, the individual may simply have to withdraw a length of the catheter which is sufficient for causing the urine to flow from the bladder. The urine will flow through the catheter conduit and into the package. The urine is allowed to drain out of the package, e.g. into the toilet or into a collection bag or reservoir connected to the package, through the opening. Preferably the opening is closed by closing means connected to the catheter for causing opening of the package upon removal of the catheter from the package. As an example, the distal end of the catheter may close the opening itself.

In order to prevent that a liquid substance being drained out of the package flows back into the package, the opening may be provided with means allowing the liquid substance to flow only in a direction out of the package. As an example, the opening may be provided with a back-flow valve. Such back-flow valves are known in the art.

According to a preferred embodiment, the closing means comprises a first valve member co-operating with a second valve member, the second valve member being attached to the catheter.

The first valve member may have a first sealing flange adapted for sealing engagement with a corresponding second sealing flange of the second valve member, the second sealing valve member thereby closing the outlet of the first valve member. The first and the second sealing flanges may then seal a passage between the hose and the surroundings outside the package.

The first valve member may further have a third sealing flange adapted for sealing engagement with a corresponding fourth sealing flange of the second valve member. The third and the fourth sealing flanges may then seal a passage between the conduit of the catheter and the surroundings outside the package.

The back-flow valve preventing liquid substances to flow back into the package may be integrated into one of either the first and/or the second valve members, e.g. in form of a sheet or flap allowed to be displaced from an opening between the package and the ambient atmosphere when a liquid flows into the reservoir, whereas the sheet or flap, by means of the liquid, is pressed back into a position wherein it blocks the passage between the ambient atmosphere and the package when liquid tends to flow in the other direction.

According to a preferred embodiment of the invention, the closing means connected to the urinary catheter is provided with a flow channel co-operating with an outlet provided in the package. In a first position of the closing means in relation to the outlet, liquid substances are allowed to flow from the conduit of the catheter and out of the package. In another position, a liquid substance is prevented to flow from the conduit of the catheter and out of the package. The two positions corresponding to a catheter respectively taken out of the package or being taken out of the package and a catheter arranged in the package.

The flow channel of the closing means may further comprise at least one inlet allowing a liquid substance to flow between the one of either the lower or upper storage compartments and the conduit of the catheter. In order to prevent year-end, trade to the catheter, from running out through the inlet, the inlet may be provided with means adapted to allow a liquid substance only to flow in the direction from one of either the lower or upper storage compartments and into the conduit.

For disabled users there may be severe difficulties in entering available toilet rooms. It is therefore an advantage to make the use of the catheter totally independent of the availability of toilet rooms by connecting a distal end of the package to a reservoir for accommodation of a liquid substance. In this case, the catheter package or at least the hose member thereof, may even be integrated in the reservoir.

It is an advantage to provide the reservoir in a material which is durable to at least moderate filling with a liquid without causing destruction of the reservoir or evaporation of the liquid substance through the walls of the reservoir. Moreover, the walls of the reservoir should at least substantially maintain its properties over a period of up to 12 or more month, e.g. up to 24 month. The reservoir could therefore preferably be made from a thermoplastic elatomeric material, other thermoplastic materials, curable elastomeric materials, polyamide resins or elastomers or any mixture thereof, i.e. the group may comprise materials like, PA, PP, PVC, PU, PE, latex, and/or Kraton™. Preferably, the reservoir is made from two foils of a sheet material joined along edges, e.g. by melting or gluing the foils together. The foils may e.g. be laminated from various materials and may e.g. comprise one layer of aluminium or a similarly metallic layer for providing a completely gas impermeable package.

DETAILED DESCRIPTION OF THE INVENTION

Preferred embodiments of the invention will now be described in details with reference to the drawing in which:

FIGS. 1a-1d shows parts of a catheter assembly according to a preferred embodiment of the present invention, FIGS. 2a-2d shows an alternative embodiment of the assembly of FIG. 1, FIGS. 3a-3e shows yet another alternative embodiment of the assembly of FIGS. 1 and 2, FIGS. 4a-4e shows an embodiment of the assembly, wherein the passage between the catheter and the hose is sealed over a first dismantling section and wherein the passage is open over a second dismantling section, FIGS. 5a-5c shows a simple embodiment of the invention, wherein the distal end of the package is closed by the distal end of the catheter itself, FIGS. 6a-6c shows an embodiment of the assembly shown in FIG. 5, wherein the distal end of the package is closed by a detachable closure, FIG. 7 shows an embodiment of an assembly comprising a reservoir for storage of urine and other liquid substances, FIG. 8 shows a perspective view of a combined valve member and a radially outwardly extending protrusion adapted to be attached to a catheter, FIG. 9 shows a cross-sectional view of the valve member of FIG. 8, FIG. 10 shows perspective view of a valve member to be fixed to an opening in the distal end of the package, and FIG. 11 shows a cross-sectional side view of the valve member of FIG. 10.

Referring to FIG. 1, a catheter assembly according to the present invention comprises a urinary catheter 1 defining a conduit 2 for transportation of urine and other liquid substances, a catheter package 3 and sealing means 4. In this respect the catheter is defined by a hose and by additional parts connected to the hose, e.g. the plug 25, cf. FIG. 2a. The plug combines the sealing between the catheter and the package and the closing means adapted to close the distal end of the package—see the following description. The catheter is provided with a proximal end 5, adapted for insertion into the urethra of an individual. The catheter is provided with holes 6 arranged peripherally around the proximal end part of the catheter for draining urine from the bladder and into the conduit of the catheter. The catheter is further provided with at least one opening 7 in the opposite distal end for draining liquid substances out of the conduit. The package is provided with a hose 9 defining a cavity 10 for accommodation of the catheter.

The sealing means 4 is arranged between the outer surface 11 of the catheter and the inner surface 12 of the hose member and provides a substantially liquid tight division of the space confined between the hose member and the catheter into a lower receptacle 13 and an upper receptacle 14.

As shown in FIG. 1, the sealing means may preferably be provided in the form of a radially outwardly extending protrusion 4, e.g. in the form of a soft, resilient vane of the catheter or attached to the catheter and provided in a length which enables the vane to contact the inner surface of the hose member.

FIG. 1a shows a preferred embodiment of the assembly, wherein a flow channel 15 is provided in order to allow a liquid substance to flow from the upper receptacle 14 and into the conduit 2, e.g. water or a water/saline solution contained in the upper receptacle for treatment of a hydrophilic catheter or a lubricant for causing a low friction surface character of a conventional catheter.

FIG. 1b shows one embodiment of the sealing means connected to the catheter.

FIG. 1c shows a situation wherein an opening 16 provided in the distal end of the package, allows liquid substances comprised in the lower receptacle to drain out of the package.

Figure 2A:
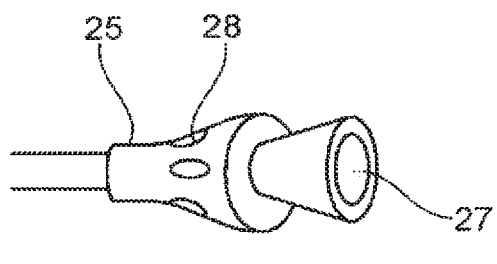
Figure 2B:
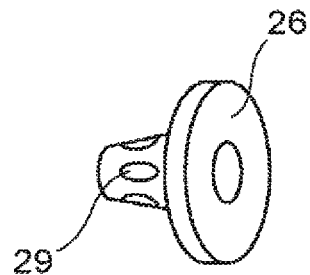

FIG. 1d shows a situation wherein closing means 17 of the catheter liquid-tightly seals the opening 16. Preferably, the closing means is provided with a number of resilient and/or soft bulges 18 adapted to contact the inner surface of the opening 16.

FIGS. 1c and 1d further shows a detachable closure 19 of the proximal end of the package. The closure may as indicated in FIGS. 1c, 1d, preferably be attached to the package via a strip 20, so that the assembly remains as one unit. The closure may be provided with a radially extending gripping handle 21, easing the removal of the closure, not least for individuals with a reduced dexterity.

FIGS. 2a, 2b, 2c and 2d shows an alternative embodiment of the plug 25 and an alternative embodiment of the distal package end, wherein an open distal end of the package is closed by a closure 26. The closure may either be detachable or glued onto the hose member 9. The plug is preferably provided with at least one outlet opening 27 allowing urine flowing from the bladder and into the proximal end of the catheter to drain out of the catheter through the plug. The plug may further be provided with an inlet 28 for draining a liquid substance from the upper receptacle 14 and into the conduit 2. The closure 26 is further provided with an opening 29 for draining liquid substances out of the lower receptacle, e.g. urine.

Figure 2C:
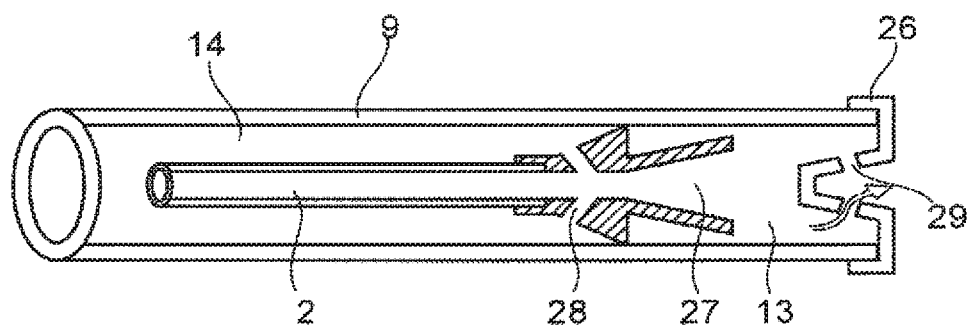

FIG. 2c shows a situation wherein the closing means of the catheter is withdrawn from the closure, whereby the passage 29 is opened.

Figure 2D:
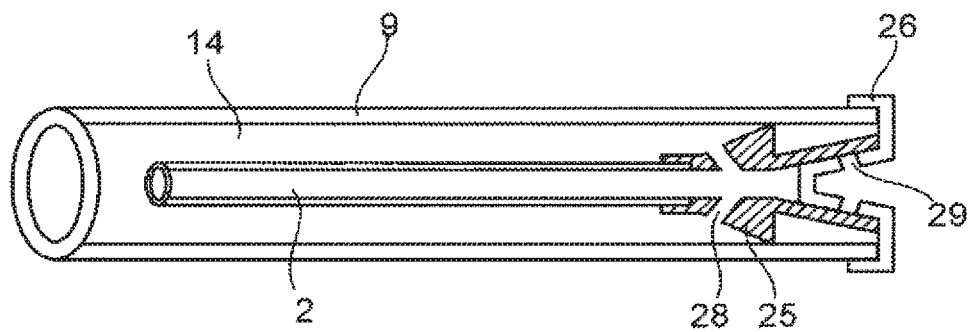

FIG. 2d shows a situation wherein the closing means of the catheter closes the passage 29 and thereby prevents a liquid substance to drain out of the package.

The catheter and package shown in FIG. 2 is not drawn in its full length. The proximal ends of both parts have been omitted in order to focus only on the differences between the embodiment of FIG. 1 and FIG. 2.

FIG. 3 shows an embodiment of the invention wherein the plug 35 is provided with features similar to the plug 25 of FIG. 2. The plug further comprises a groove 36 adapted to engage a ring shaped sealing member 37. The ring shaped sealing member is provided inside the package 38, either fixed to the inner surface of the hose or movably arranged so that it is allowed to slide back and fourth in the hose.

Figure 3A:
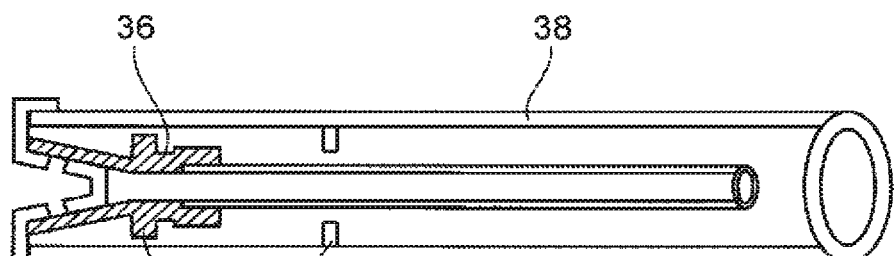
Figure 3B:
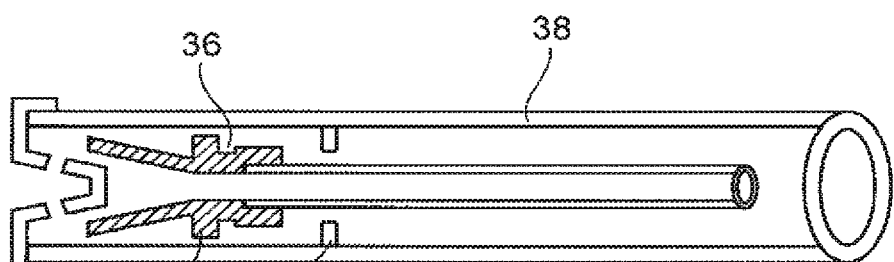
Figure 3C:
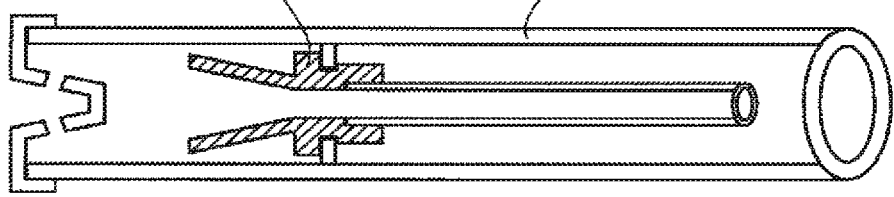
Figure 3D:
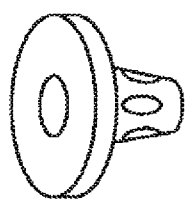
Figure 3E:
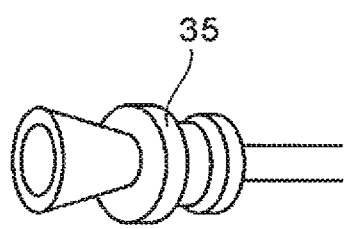
Figure 4A:
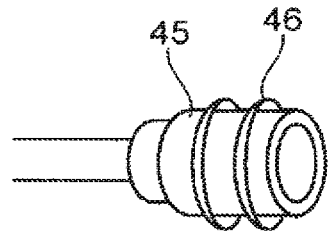
Figure 4B:
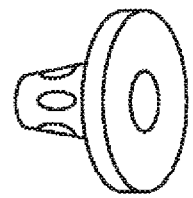
Figure 4C:
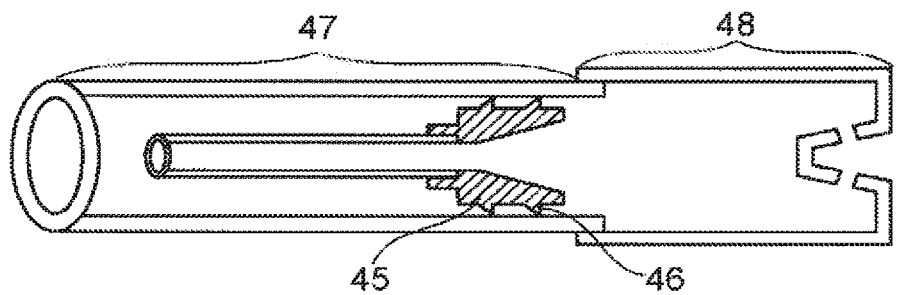
Figure 4D:
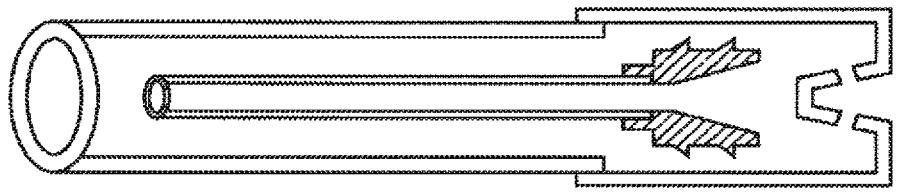
Figure 4E:
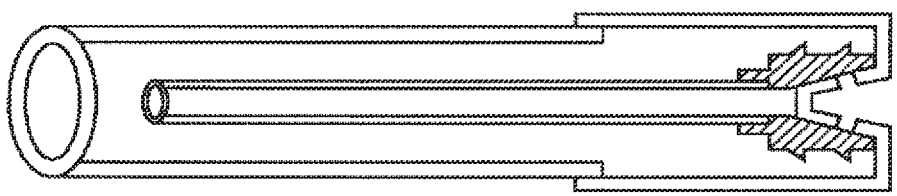

FIG. 3c shows a situation wherein the ring shaped member engages the groove. Likewise the embodiment of FIG. 2, the proximal ends of both the catheter and the package have been left out intentionally in order to focus only on the differences between the embodiment of FIG. 2 and FIG. 3.

FIG. 4 shows an embodiment of the invention where the plug 45 is provided with resilient vanes 46 provided with a diameter so that they over a first section 47 of the hose may contact the inner surface, when the plug is positioned within this section of the hose. The hose is provided with two different radial sizes. Accordingly, since the radial size of a second section 48 of the hose is larger than the radial size of the first section of the hose, the vanes 46 can not contact the inner surface of the hose, when the plug is positioned within the second section.

Figure 5A:
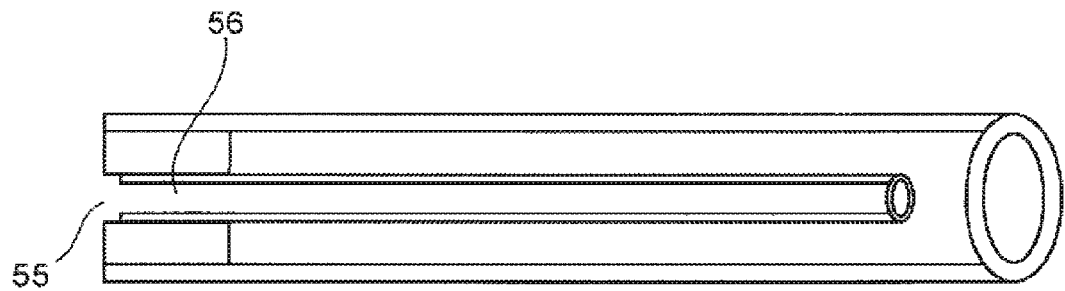
Figure 5B:
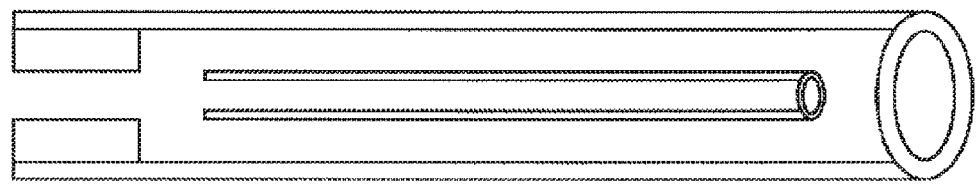
Figure 5C:

FIG. 5 shows a simple embodiment of the invention wherein the package in its distal end is provided with an opening 55. The opening may be closed by the distal end 56 of the catheter itself, whereby the distal end of the package is automatically opened upon removal of the catheter from the catheter package. As indicated, a liquid substance comprised in the package, e.g. a liquid swelling medium for treatment of a hydrophilic catheter, is allowed to drain out of the package through the holes 57 provided in the proximal end of the catheter. The proximal end of the catheter and package is, for simplification of the drawing, left out of the FIGS. 5a and 5b. In FIG. 5c, the proximal end of the package is left out. However, the proximal end of the package may be closed e.g. by a closure of any kind.

Figure 6A:
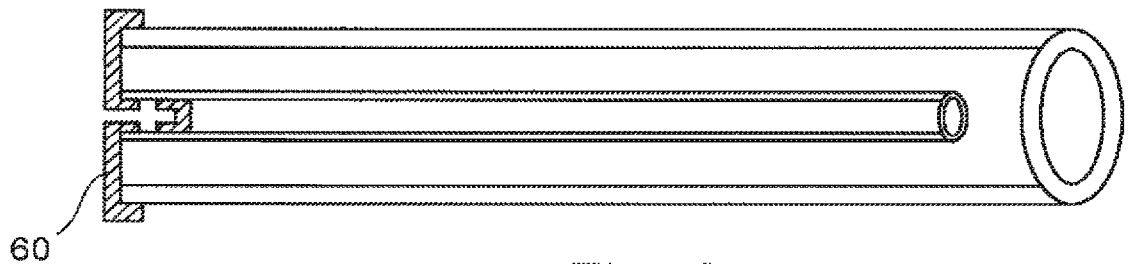
Figure 6B:
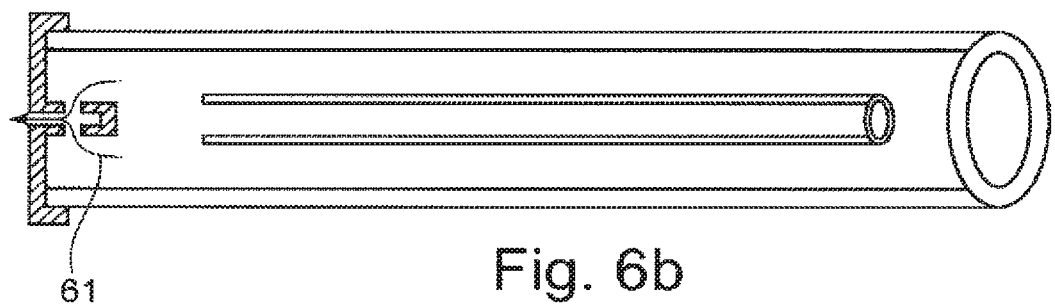
Figure 6C:
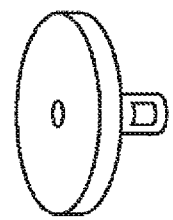

FIG. 6 shows an embodiment of the invention, wherein the distal end of the package is closed by a detachable closure 60. The closure is provided with an outlet 61 for draining liquid substances out of the package. In a first position of the catheter in relation to the package and the closure, see FIG. 6a, the outlet is closed by the distal end of the catheter. When the catheter is removed from the package, the outlet is opened, whereby liquid substances is drained out of the package.

Figure 7:
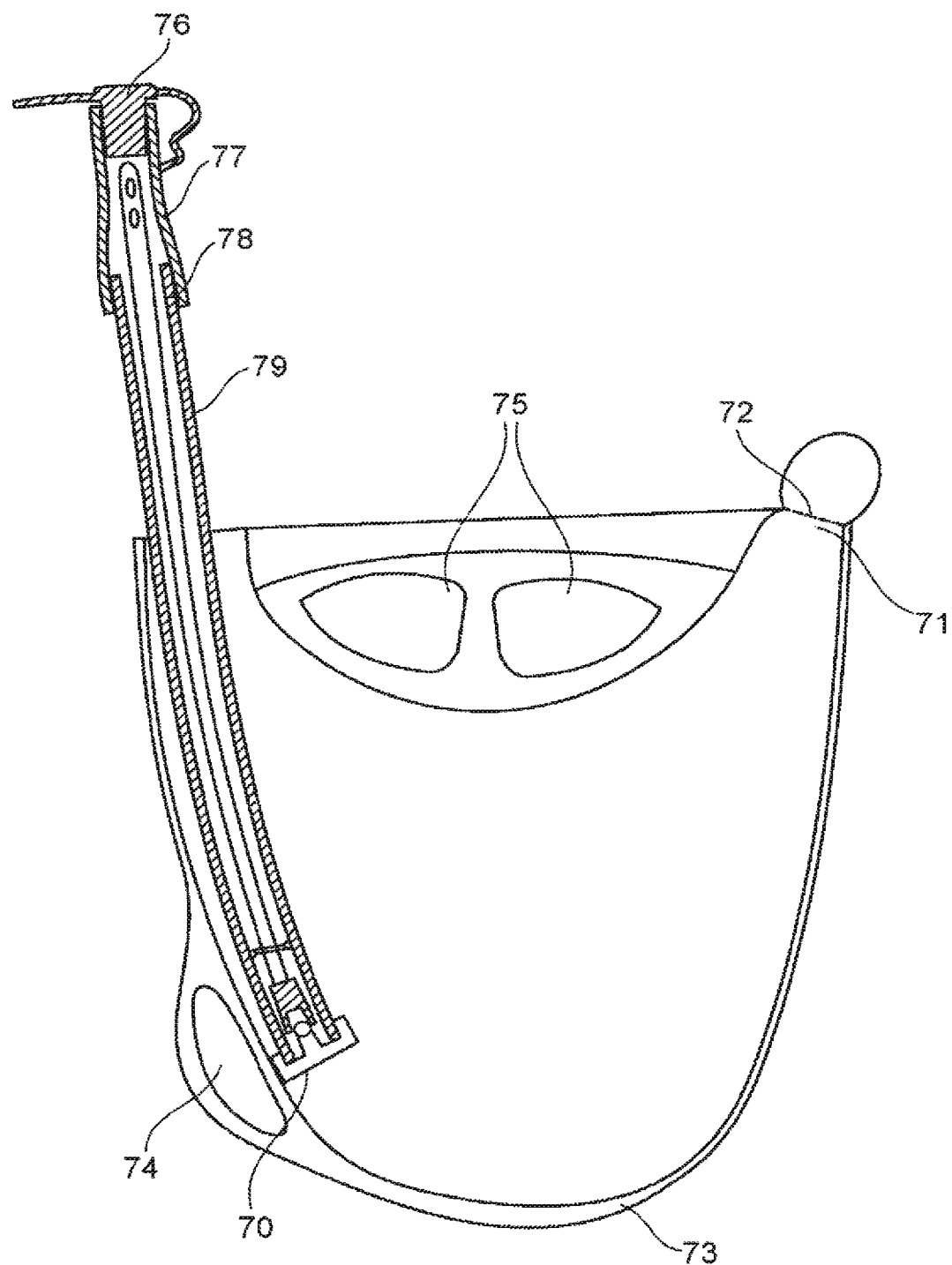

FIG. 7 shows an embodiment of the invention wherein the hose member is connected to a reservoir for collection of liquid substances, e.g. for collection of urine and/or a saline solution having been used for establishing a low friction surface character of the catheter prior to use. The valve 70 may preferably be provided as a one-way closure, so as to ensure that liquids drained into the reservoir does not flow back through the hose member and/or through the catheter. The reservoir is provided with a draining spout or valve 71 for draining the liquid substances out of the reservoir. As an example, the draining valve may be opened by tearing off a top part of the valve. For this purpose the reservoir may preferably be provided with a weakening line 72. The reservoir may preferably be formed as a bag with a substantially flat bottom part 73. Thereby it will be possible for the user to leave the reservoir on a flat surface, e.g. on the floor, while the catheter is inserted into the urethra and while urine is drained into the reservoir. Instructions relating to the opening of the draining valve may preferably be printed on the reservoir. The handles 74, 75 give the user a better grip, e.g. when emptying the reservoir. For this purpose, it will be specifically appropriate to use both handles in combination, so that the reservoir is lifted in the top handles 75, while the rear handle 74 is used to rotate the reservoir. In this respect, it should be kept in mind that the user would typically be at least partly motorically disabled. The assembly further comprises a closure 76 for opening and closing the assembly, respectively. In the embodiment of FIG. 7, the compartment 77 is joined telescopically to the hose 79 via the joint 78.

Figure 8:
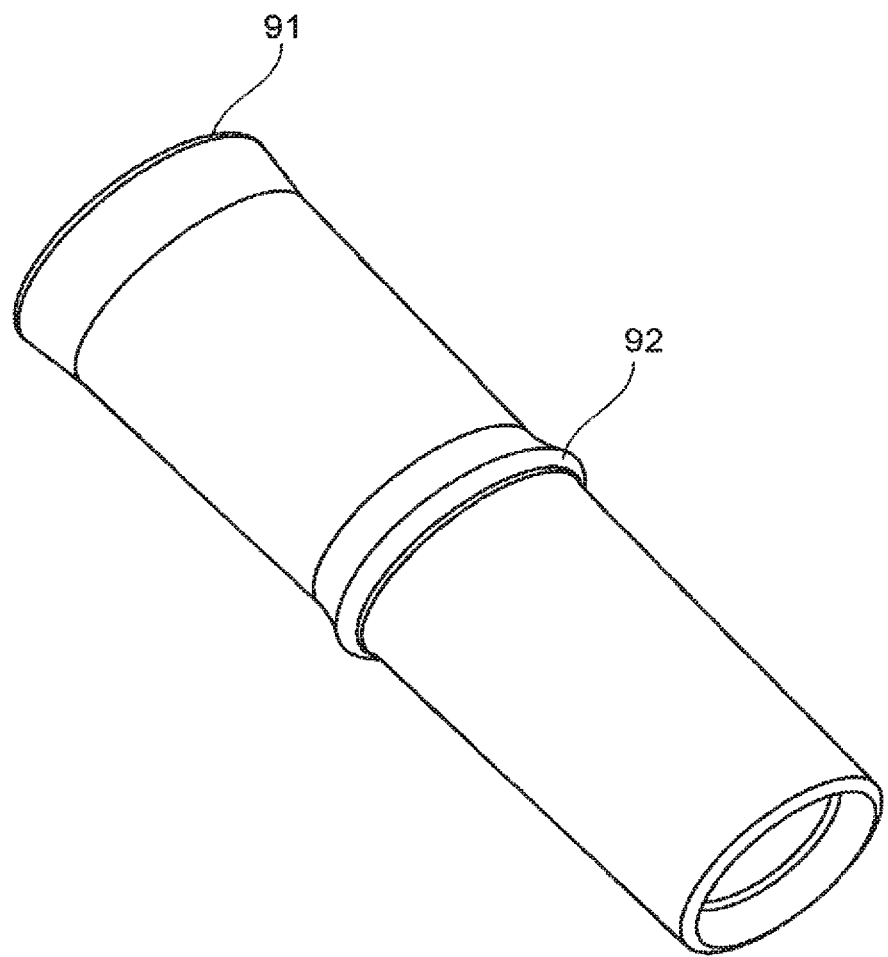
Figure 9:
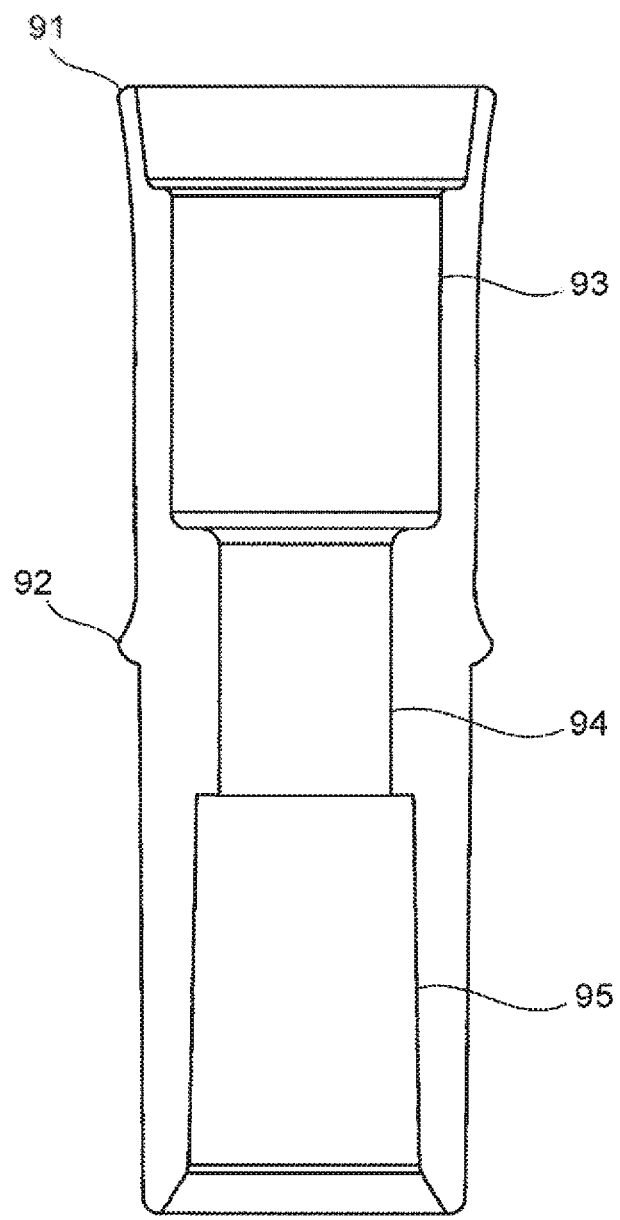

FIG. 8 shows a view of a second valve member in the form of a combined valve member and a radially outwardly extending protrusion. The second valve member is adapted to be attached to a distal end of a catheter. The catheter member is on the outer surface provided with a sliding seal 91 (a piston seal) and a locking ring 92. The inner surface, which is best seen in FIG. 9, is provided with a second sealing flange 93 and a fourth sealing flange 94.

Figure 10:
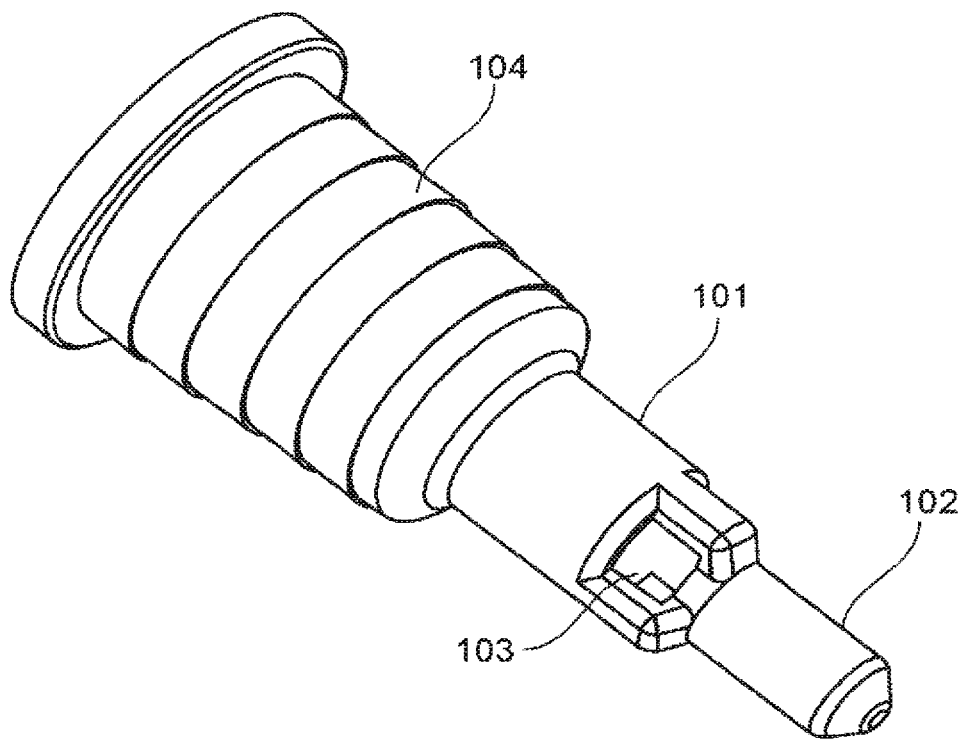
Figure 11:
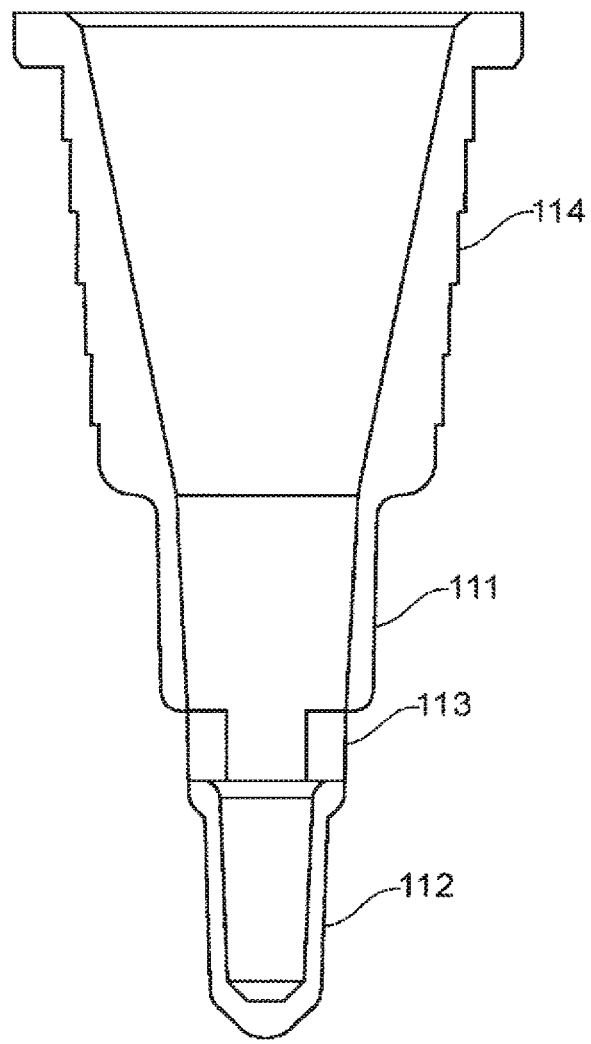

FIG. 10 shows a first valve member of the package. The valve member should be attached in an opening of the distal end of the package. The first valve member is adapted to engage the corresponding second valve member of the catheter, cf. FIGS. 8 and 9. Through the sealing engagement between the first sealing flange 101 of the first valve member, c.f. FIG. 10, and the second sealing flange 93 of the second valve member, a passage between the package or hose and the surroundings may be sealed. Through the sealing engagement between the third sealing flange 102 of the first valve member, c.f. FIG. 10, and the fourth sealing flange 93 of the second valve member, a passage between the conduit of the catheter and the surroundings may be sealed. When the catheter is removed from the package, or in fact already when a first part of the catheter is removed from the package, the second valve member is removed from the first valve member. Accordingly, the sealing engagement between the sealing flanges is removed and liquid substances both from the package and from the conduit of the catheter may flow out through the hole. The inner sealing flange 95 of the second valve member, c.f. FIG. 9, is provided for attaching the second valve member to a catheter, e.g. by adhesively bonding the valve to the outer surface of the distal catheter end. The catheter could also be moulded in one piece with an integrated valve part with features similar to the features of the valve of FIG. 9. The stepped configuration 104, 114 of the first valve member, c.f. FIGS. 10 and 11 is provided to support sealing engagement between the outer surface of the stepped part of the valve member and an inner surface of a hose of a catheter package. The first valve member may be adhesively bonded to the hose or the hose may be moulded in one piece with an integrated valve part with the features similar to the features of the valve of FIGS. 10 and 11.

The invention claimed is:

1. A catheter assembly comprising:

a urinary catheter defining a conduit having a proximal end that is insertable into a bladder and an opposing distal end portion; and a catheter package containing the urinary catheter, the catheter package having a proximal end defining a first opening adapted for dispensing the proximal end of the urinary catheter and a distal end defining a second opening provided to drain liquid out of the catheter package;

wherein the urinary catheter seals between an outer surface of the urinary catheter and an inner surface of the catheter package along a longitudinal length of the catheter package extending between the distal end of the catheter package toward the proximal end of the catheter package while the urinary catheter is dismantled from the catheter package to expose a length of the urinary catheter sufficient for insertion into the bladder.

* * * * *